(12) United States Patent
Minium

(10) Patent No.: US 7,731,496 B2
(45) Date of Patent: Jun. 8, 2010

(54) ADJUSTABLE ORTHODONTIC APPARATUS

(76) Inventor: Mark Minium, 1141 Dry Powder Cir., Mechanicsburg, PA (US) 17050

( * ) Notice: Subject to any disclaimer, the term of this patent is extended or adjusted under 35 U.S.C. 154(b) by 188 days.

(21) Appl. No.: 11/982,199

(22) Filed: Nov. 2, 2007

(65) Prior Publication Data
US 2009/0117508 A1 May 7, 2009

(51) Int. Cl.
A61C 7/00 (2006.01)
A61C 7/14 (2006.01)

(52) U.S. Cl. .......................... 433/24; 433/16
(58) Field of Classification Search ............... 433/8–16, 433/24
See application file for complete search history.

(56) References Cited

U.S. PATENT DOCUMENTS

| | | | |
|---|---|---|---|
| 2,379,011 A | 6/1945 | Laskin | |
| 3,203,098 A | 8/1965 | Petraitis | |
| 3,218,712 A | 11/1965 | Wallshein | |
| 3,421,221 A | 1/1969 | Silverman et al. | |
| 3,423,833 A | 1/1969 | Pearlman | |
| 3,461,559 A | 8/1969 | Silverman et al. | |
| 3,464,113 A | 9/1969 | Silverman et al. | |
| 3,721,005 A | 3/1973 | Cohen | |
| 3,946,488 A | 3/1976 | Miller et al. | |
| 4,139,945 A | 2/1979 | DiGiulio | |
| 4,161,066 A | 7/1979 | Morrow et al. | |
| 4,243,387 A | 1/1981 | Prins | |
| 4,353,692 A | 10/1982 | Karrakussoglu | |
| 4,487,580 A | 12/1984 | Ridgeway | |
| 4,487,581 A | 12/1984 | Adler | |
| 4,597,739 A | 7/1986 | Rosenberg | |
| 4,676,746 A | 6/1987 | Klapper | |
| 4,867,678 A | 9/1989 | Parker | |
| 4,917,602 A | 4/1990 | Broussard | |
| 5,954,502 A | 9/1999 | Tuenge et al. | |
| 6,190,166 B1 | 2/2001 | Sasakura | |
| 7,431,586 B1 * | 10/2008 | Silverman | 433/9 |
| 2006/0008761 A1 | 1/2006 | Allred | |
| 2007/0092849 A1 * | 4/2007 | Cosse | 433/8 |

* cited by examiner

Primary Examiner—Cris L Rodriguez
Assistant Examiner—Michael R Ballinger (57) ABSTRACT

An adjustable orthodontic apparatus formed by at least one base plate having opposing sides, the first side being a tooth engaging side and the second side having a plurality of columns of protrusions and channels created by the columns of protrusions and at least one connecting plate having opposing sides, the first side having a plurality of columns of protrusions and channels created by the columns of protrusions. The protrusions are designed to travel within the channels during an adjustment stage. A securing device locks the connecting plate to a desired position on the base plate.

13 Claims, 12 Drawing Sheets

ADJUSTABLE ORTHODONTIC APPARATUS

BACKGROUND OF THE INVENTION

1. Field of the Invention

This invention relates to an adjustable orthodontic device and more particularly, a orthodontic apparatus with a base plate, a vertically and horizontally adjustable connecting plate and a device for locking the base plate to the connecting plate.

2. Description of the Related Art

The Science of Orthodontics has been advancing at a rapid pace in the past several years. High-tech alloy wires, used in applying orthodontic forces to teeth, were previously only available in stainless steel. The more flexible "memory" wires of today employ the use of titanium, niobium, copper and other more efficient materials. These heat activated wires allow for lower longer acting forces with more allowable deflection of the wire to engage malpositioned teeth. Wires themselves have been tied into the brackets first by steel ligatures, then elastometric ties, and most recently by self closing "doors".

Bracket placement has always been important in Orthodontics, and the introduction of the self-ligating brackets has only stood to increase its importance. Since bracket position directly effects the force application of the archwire and ultimately the final position of the tooth, much has been said about correctly placing brackets during treatment. Positioning instruments have been devised, indirect bonding has been useful in certain cases and most recently, computer aided indirect bonding has been devised which attempts to predict the final tooth position based on a recommended bracket position.

Even using the newest and most advanced types of orthodontic brackets still requires a visit to be scheduled about 6 months after the initial application of the brackets. This appointment is focused on repositioning the brackets using a panorex to help parallel roots and improve bracket position. This "pano-repo" visit is done on all patients and may be necessary more than once during their treatment thereby requiring multiple visits to the orthodontist.

Specifically, a patient is reappointed in 6-8 weeks for a 45 minute appointment. During this visit, an average of 4-6 brackets are removed and discarded. Cement is cleaned off the tooth; the teeth are then etched, sealed, re-bracketed with new brackets and retied. The significance of this visit is that sliding reduced friction mechanics do not work if the archwire has bends in it and the high tech memory wires cannot be bent. Tooth positioning is extremely dependent upon ideal bracket positioning.

To overcome these problems, the present invention provides for a design for a bracket and pad connector that allows the bracket to be repositioned on the base without having to remove the cemented base from the tooth.

The connector of the present invention can be used on any bracket design and creates an interface between the bracket pad or base which is glued to the tooth and the bracket archwire slot itself. The archwire slot of the present invention may be either the standard style design or self ligating design.

Unlike the prior art, the connector of the present invention is strong, simple to use and allows for multiple options in bracket positioning both vertically and horizontally. Application of this connector would reduce the need to reposition brackets by recementation, and should help to reduce or eliminate the need to place compensating bends in the orthodontic archwires during treatment. The present invention would also reduce chair time requirements as well as increase treatment efficiency enabling patients to complete treatment in less time.

SUMMARY OF THE INVENTION

In one embodiment, the present invention relates to an adjustable orthodontic apparatus comprising: a base plate comprising opposing sides, a first side being a tooth engaging side and a second side comprising a first device for engaging and adjusting the vertical and horizontal position of a connecting plate; the connecting plate having opposing sides, a first side comprising a second device for engaging the second side of the base plate and allowing for the vertical and horizontal movement of the connecting plate as it relates to the base plate; and a securing device for locking the connecting plate to a desired position onto the base plate.

In another embodiment, the securing device for locking said base plate to the connecting plate comprises a pin. In one embodiment, the pin comprises a rod with a ball hook on one of its ends. In another embodiment, the pin may be straight elongated rod or pin.

In yet another invention, the apparatus further comprises an orthodontic device and wherein a second side of the connecting plate comprises a surface for attaching the orthodontic device to the connecting device. In still another embodiment, the orthodontic device is selected from a group consisting essentially of an archwire receiving bracket, an archwire receiving eyelet, springs, elastomeric hooks and mixtures thereof. For purposes of this invention, a bracket is defined as a device which is attached to the surface of a tooth designed for attachment of archwires or auxiliaries such as springs or elastics and for the transmission of forces from these archwires or auxiliaries to the teeth and their supporting structures. In most cases, tooth moving forces are stored in archwires and delivered through brackets to the tooth and periodontium by deflection of the archwire from a passive to an active state. In other situations, tooth moving forces are generated by auxiliaries such as springs or elastics and are transmitted through the archwire to the fixed portions of the appliance and hence to the periodontium.

In addition, a bracket comprises: a base which is either bonded to the tooth by incorporating a mesh pad on the back of the bracket that bonding cement is mechanically puttied into and then adheres to the tooth or is welded or brazed to a band which is cemented around a tooth; one or more archwire slots designed for receiving the archwires; and occlusal and gingival flanges or wings designed to receive elastic or metal ligatures used in holding the archwire into the slot. Self ligating brackets incorporate a sliding door that closes over the slot holding the wire in place.

In still another embodiment, the first device of the second side of the base plate comprises at least two vertically positioned protrusions and at least two horizontally positioned protrusions and the second device of the first side of the connecting plate comprises at least two vertically positioned protrusions and at least two horizontally positioned protrusions. In still yet another embodiment, there are a plurality of spaces in between each of the protrusions in the second side of the base plate and the first side of the connecting plate, the plurality of spaces provides for channels for protrusions to move during adjustment of the connecting plate relative to the base plate and the securing device is situated within the channel when the connecting plate is locked onto the base plate.

In a further embodiment, the first device of the second side of the base plate comprises a plurality of vertical and horizontal column of protrusions and the second device of the first side of the connecting plate comprises a plurality of vertical and horizontal column of protrusions, and the plurality of column of protrusions provides for a plurality of vertical and horizontal channels.

In another further embodiment, the channels provides the protrusion to move during adjustment of the connecting plate relative to the base plate and the securing device is situated within the channel when the connecting plate is locked into a certain position relative to the base plate. In yet a further embodiment, the protrusions are designed to move vertically and horizontally within said channels during the adjustment of the connecting plate relative to the base plate. In still a further embodiment, the at least one of the protrusions of the connecting plate and at least one of the protrusions of the base plate engage one another when the securing device locks the connecting plate to the base plate.

In still yet a further embodiment, the tooth engaging side of the base plate is generally concave to conform with the curvature of a tooth. In still yet another further embodiment, the protrusions of the base plate and the second device have geometric shapes, and at least one of the protrusions of the base plate has a geometric shape that creates a retentive undercut with the opposing geometric shape of the second device.

In another embodiment, the present invention provides for an adjustable orthodontic apparatus comprising: at least one base plate comprising opposing sides, a first side being a tooth engaging side and a second side comprising a plurality of vertical and horizontal columns of protrusions and plurality of vertical and horizontal channels created by the columns of protrusions; at least one connecting plate having opposing sides, a first side comprising a plurality of vertical and horizontal columns of protrusions and plurality of vertical and horizontal channels created by the columns of protrusions, and the protrusion designed to travel vertically and horizontally within said channel during an adjustment stage; and a securing device for locking said connecting plate to a desired position onto said base plate.

In yet another embodiment, the securing device for locking the base plate to the connecting plate comprises a pin. In still another embodiment, the apparatus further comprises an orthodontic device and wherein a second side of the connecting plate comprises a surface for attaching the orthodontic device to the connecting plate. In still a further embodiment, the second side of the connecting plate comprises an orthodontic device.

In still yet another embodiment, the orthodontic device is selected from a group consisting essentially of an archwire receiving bracket, an archwire receiving eyelet, spring, hook, elastomeric hook and mixtures thereof. In a further embodiment, at least one of the protrusions of the connecting plate and at least one of the protrusions of the base plate engage one another when the securing device locks the connecting plate to the base plate.

In another further embodiment, the present invention relates to an adjustable orthodontic system comprising: a plurality of orthodontic apparati comprising at least one base plate comprising opposing sides, a first side being a tooth engaging side and a second side comprising a plurality of vertical and horizontal columns of protrusions and plurality of vertical and horizontal channels created by the columns of protrusions; at least one connecting plate having opposing sides, a first side comprising a plurality of vertical and horizontal columns of protrusions and plurality of vertical and horizontal channels created by the columns of protrusions, and the protrusion is designed to travel vertically and horizontally within the channel during an adjustment stage, a second side comprising an orthodontic device; and a device for securing and locking said connecting plate to a desired position onto the base plate.

In yet another embodiment, the plurality of said apparati are attached to a patient's teeth and each apparati are adjusted vertically and horizontally to desired positions, then locked into said desired position using the securing means and braces are then attached to each of the apparati. In still another embodiment, the device for securing and locking the base plate to the connecting plate comprises a pin. In still yet another embodiment, the orthodontic device is selected from a group consisting essentially of an archwire receiving bracket, an archwire receiving eyelet, springs, hooks and mixtures thereof.

In another further embodiment, the connector of the present invention could be cast, milled or injection molded as part of existing bracket designs (traditional or self ligating) and would greatly enhance their mechanical ability to align teeth. The present invention may also be used with all ceramic and composite bracket designs as well as stainless steel or titanium or other metal brackets.

BRIEF DESCRIPTION OF THE DRAWINGS

The accompanying drawings are included to provide a further understanding of the present invention. These drawings are incorporated in and constitute a part of this specification, illustrate one or more embodiments of the present invention, and together with the description, serve to explain the principles of the present invention.

Among those benefits and improvements that have been disclosed, other objects and advantages of this invention will become apparent from the following description taken in conjunction with the accompanying drawings. The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention that may be embodied in various forms. The figures are not necessary to scale, some features may be exaggerated to show details of particular components. Therefore, specific structural and functional details disclosed herein are not to be interpreted as limiting, but merely as a basis for the claims and as a representative basis for teaching one skilled in the art to variously employ the present invention.

Figure 1:
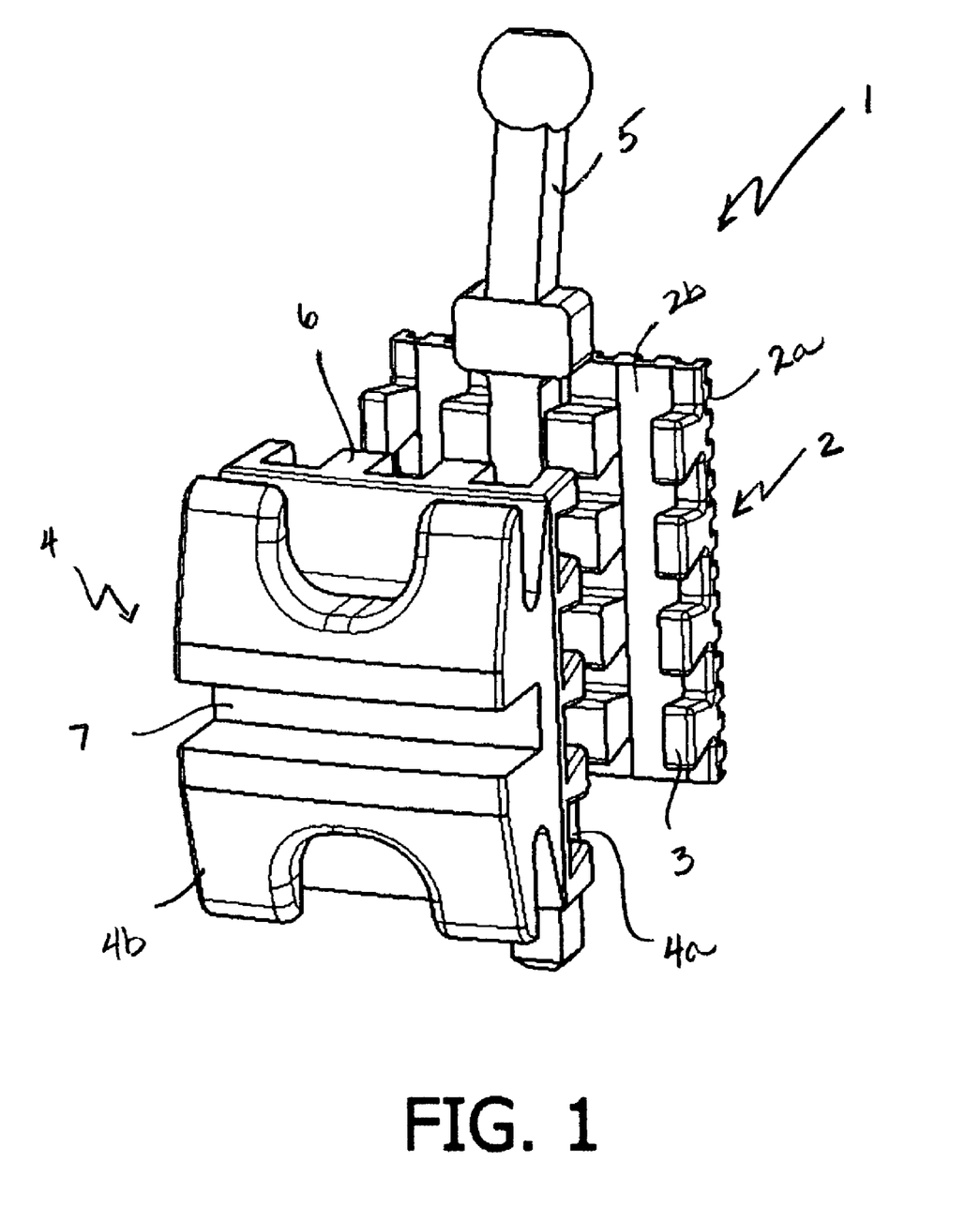
FIG. 1 is an exploded view of one of the embodiments of the present invention.
Figure 2:
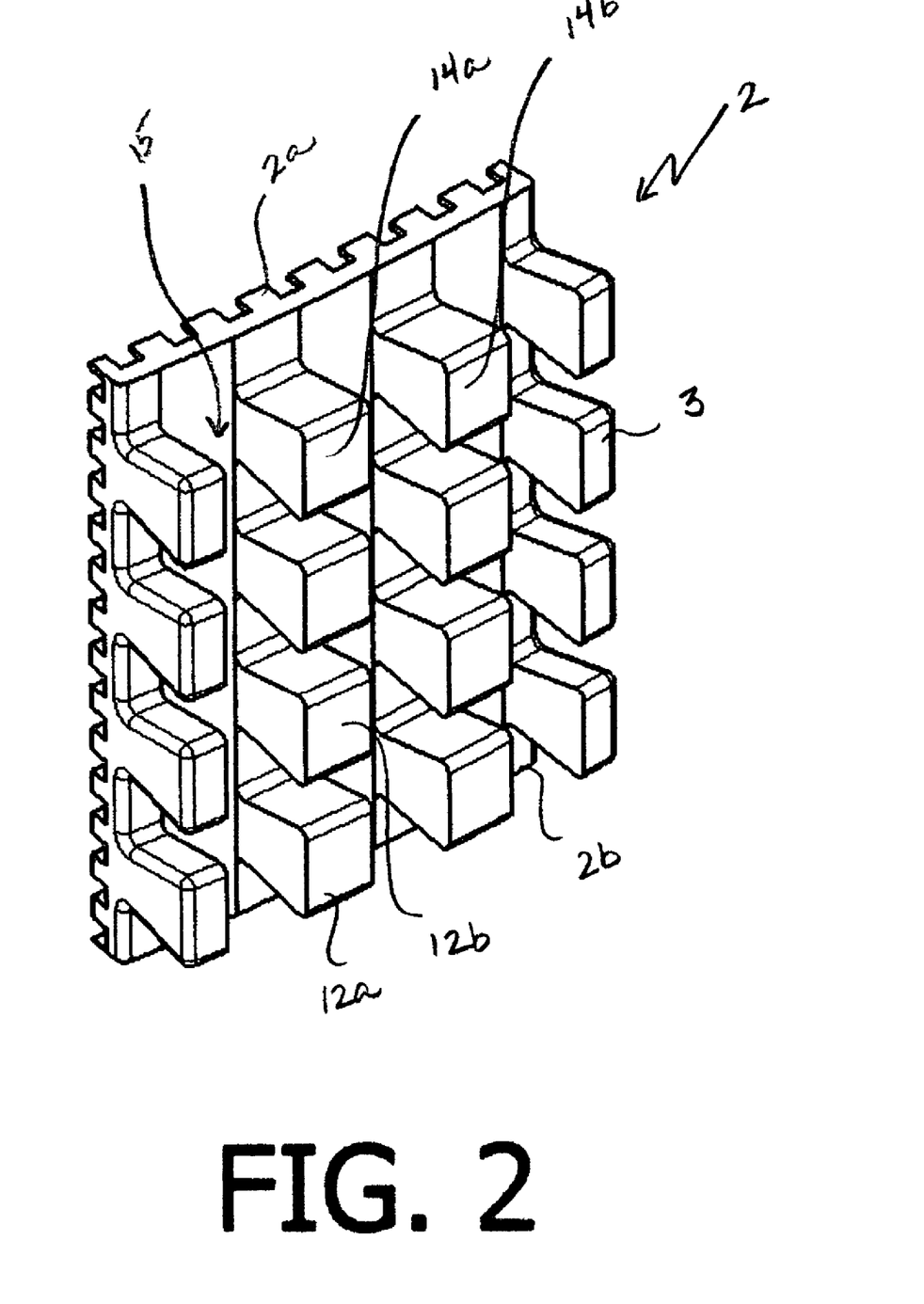
FIG. 2 is a front perspective view of one of the embodiments of the base plates of the present invention.
Figure 3:
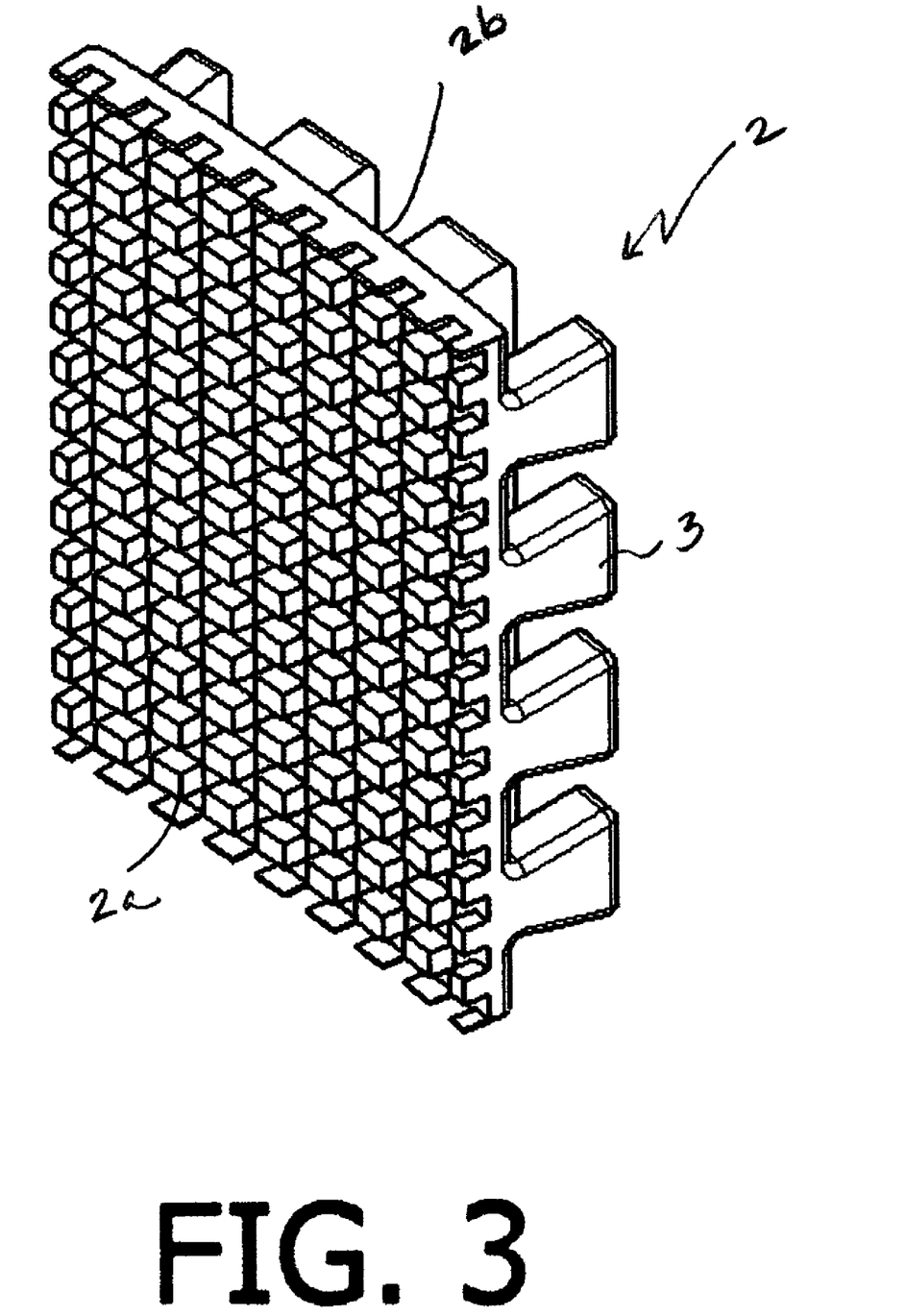
FIG. 3 is a back perspective view of the base plate in FIG. 2.
Figure 4:
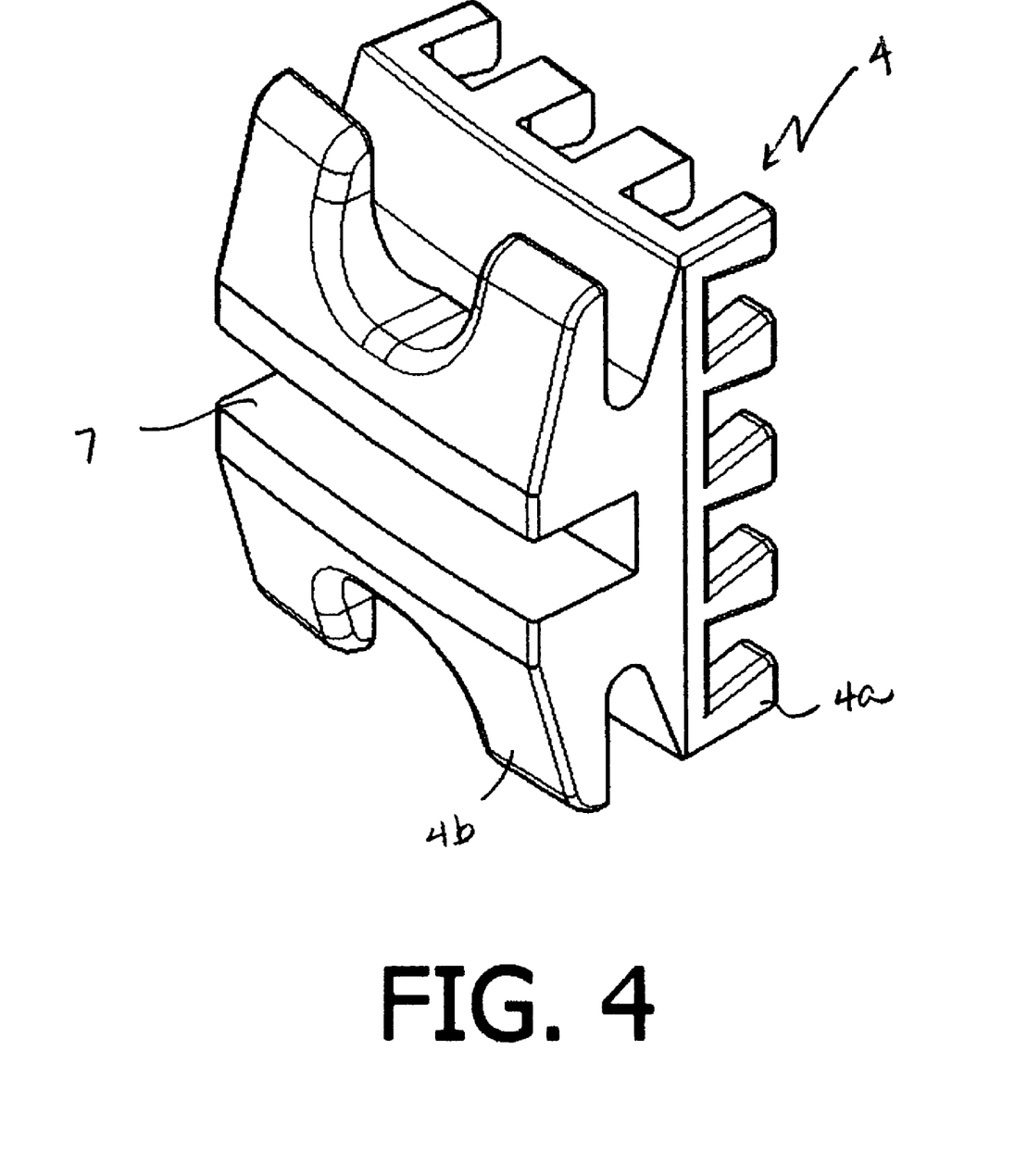
FIG. 4 is a frontal perspective view of one of the embodiments of the connecting plate of the present invention.
Figure 5:
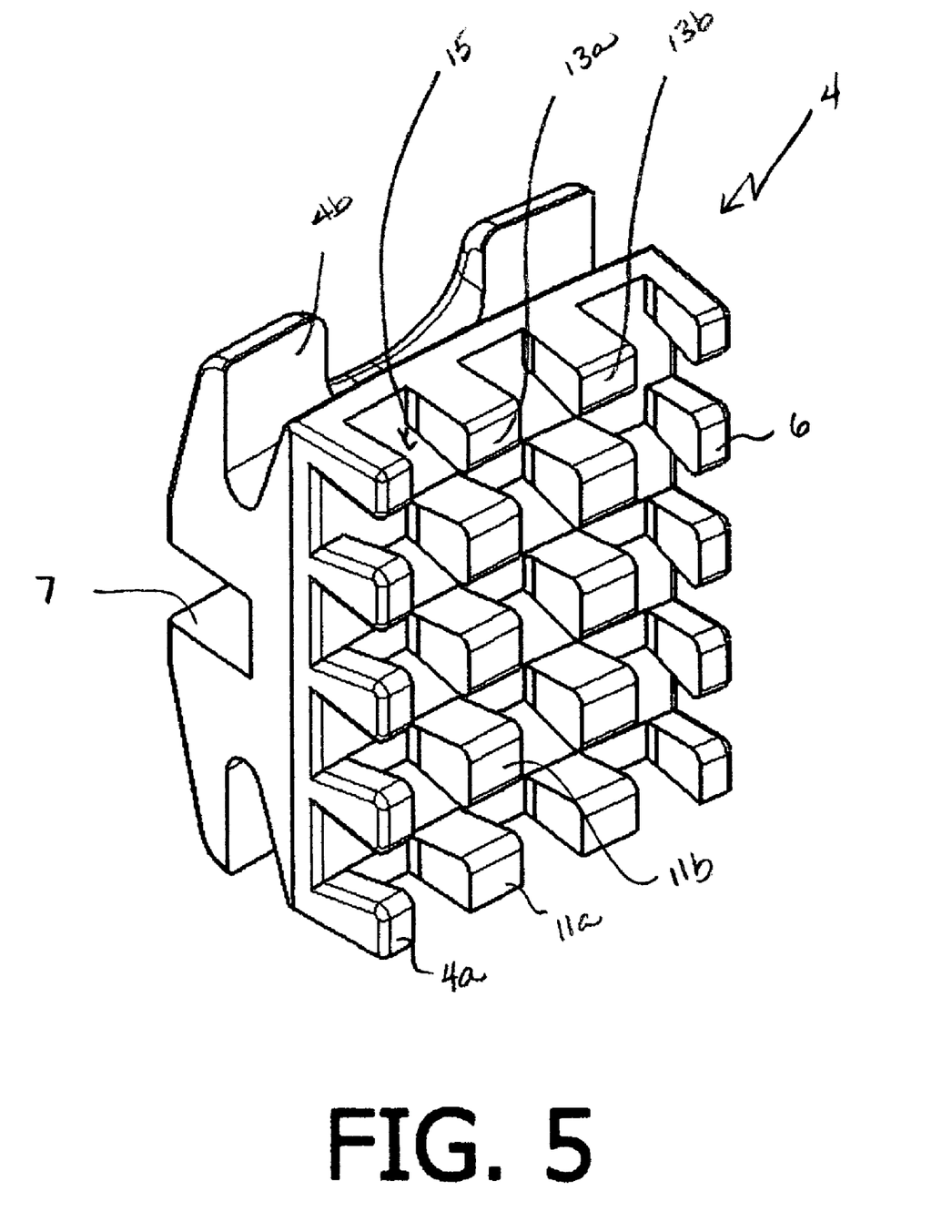
FIG. 5 is a back perspective view of the connecting plate in FIG. 4.

FIG. 1 illustrates one of the embodiments of the present invention, more specifically, an adjustable orthodontic apparatus 1 is provided. The apparatus 1 comprises: a base plate 2 comprising opposing sides, 2a and 2b respectively, a first side 2a being a tooth engaging side and a second side 2b comprises a first device 3 for engaging and adjusting the vertical and horizontal position of a connecting plate 4. The connecting plate 4 has opposing sides, 4a and 4b respectively, a first side 4a comprises a second device 6 for engaging the second side 2b of the base plate 2 and allowing for the vertical and horizontal movement of the connecting plate 4 as it relates to the base plate 2. The apparatus 1 further comprises a securing device 5 for locking the connecting plate 3 to a desired position onto the base plate 2.

The securing device 5 for locking the base plate 2 to the connecting plate 3 comprises a pin. The second side 4b of the connecting plate 4 comprises an orthodontic device 7. The orthodontic device 7 may be an archwire receiving bracket or an archwire receiving eyelet.

FIGS. 2-5 relate to the front and back views of the base plate 2 and connecting plate 4 of the present invention. The first device 3 of the second side 2b of the base plate 2 comprises at least two vertically positioned protrusions, 12a and 12b respectively, and at least two horizontally positioned protrusions, 14a and 14b respectively, and the second device 6 of the first side 4a of the connecting plate 4 comprises at least two vertically positioned protrusions, 11a and 11b respectively, and at least two horizontally positioned protrusions, 13a and 13b respectively.

There are a plurality of spaces in between each of the protrusions, 11a, 11b, 12a, 12b, 13a, 13b, 14a and 14b respectively, in the second side 2b of the base plate 2 and the first side 4a of the connecting plate 4. The plurality of spaces provides for channels 15 for protrusions, 11a, 11b, 12a, 12b, 13a, 13b, 14a and 14b respectively, to move during adjustment of the connecting plate 4 relative to the base plate 2 and the securing device 5 is situated with the channel 15 when the connecting plate 4 is locked onto the base plate 2.

Figure 6:
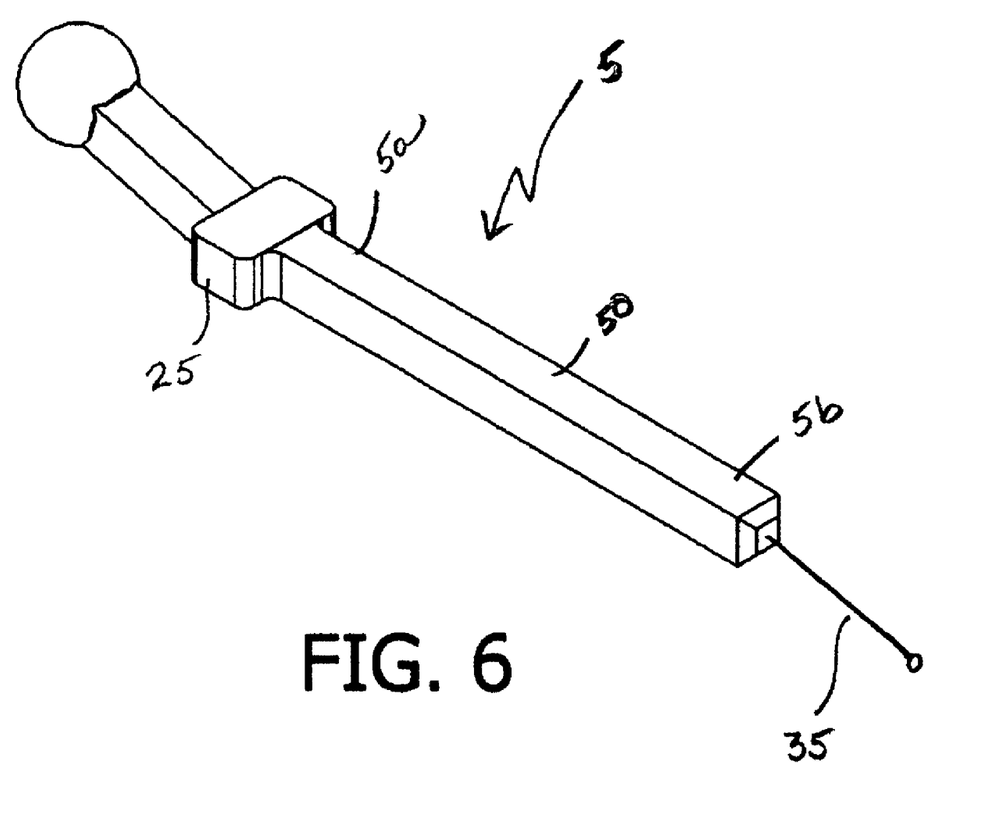
FIG. 6 is a perspective view of the securing device of the present invention.

FIG. 6 illustrates the securing device 5 which comprises an elongated shaft 50 designed to fit within the channels between the protrusions and also has opposing ends, 5a and 5b respectively. One side 5a has extended stop portion 25 and the opposing side 5b has a bendable portion 35 designed to lock the position of the connecting plate to the base plate. In another embodiment, side 5a is lightly bent at an angle.

Figure 7:
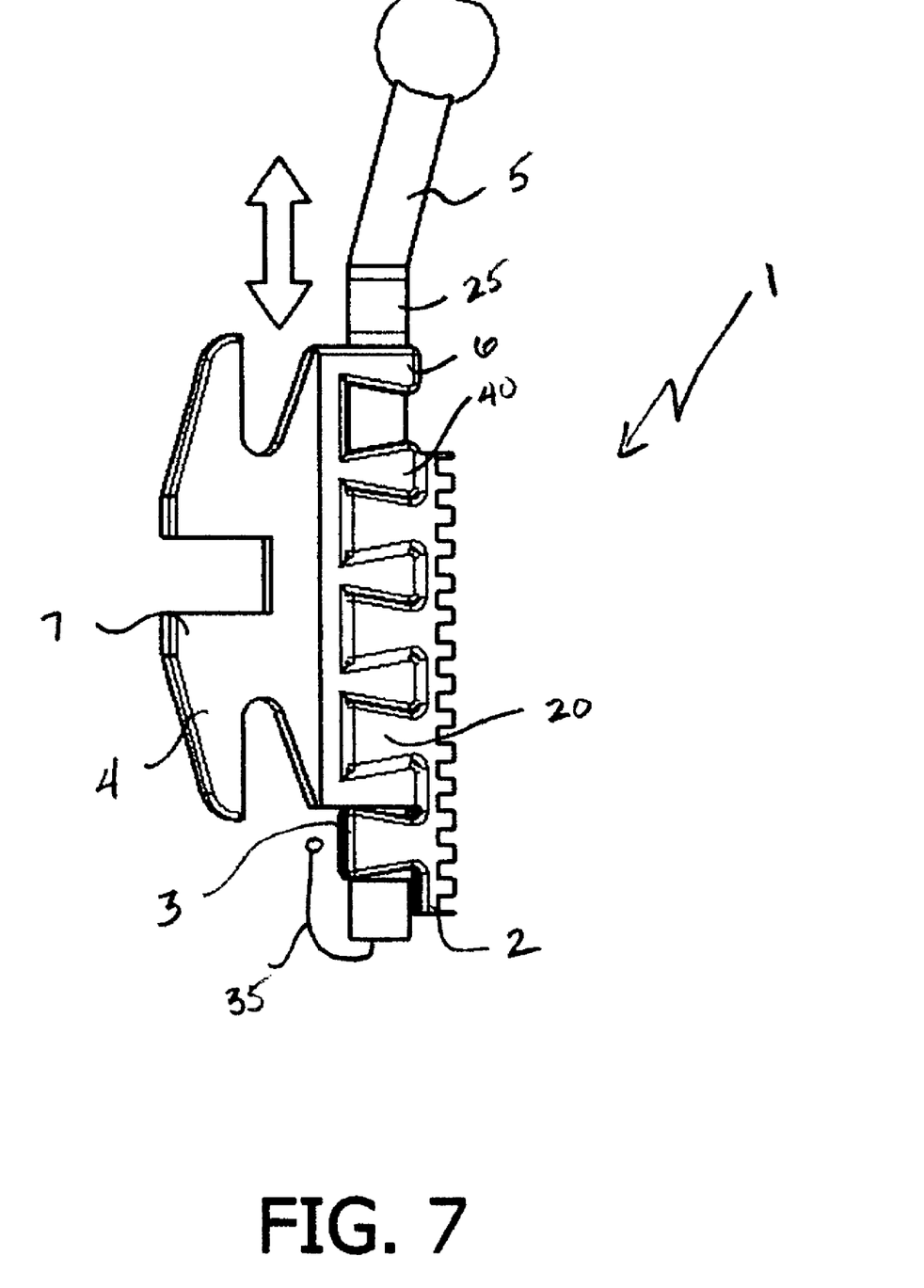
FIG. 7 is a side perspective view of the interaction of the connecting plate and the base plate of the present invention.
Figure 8:
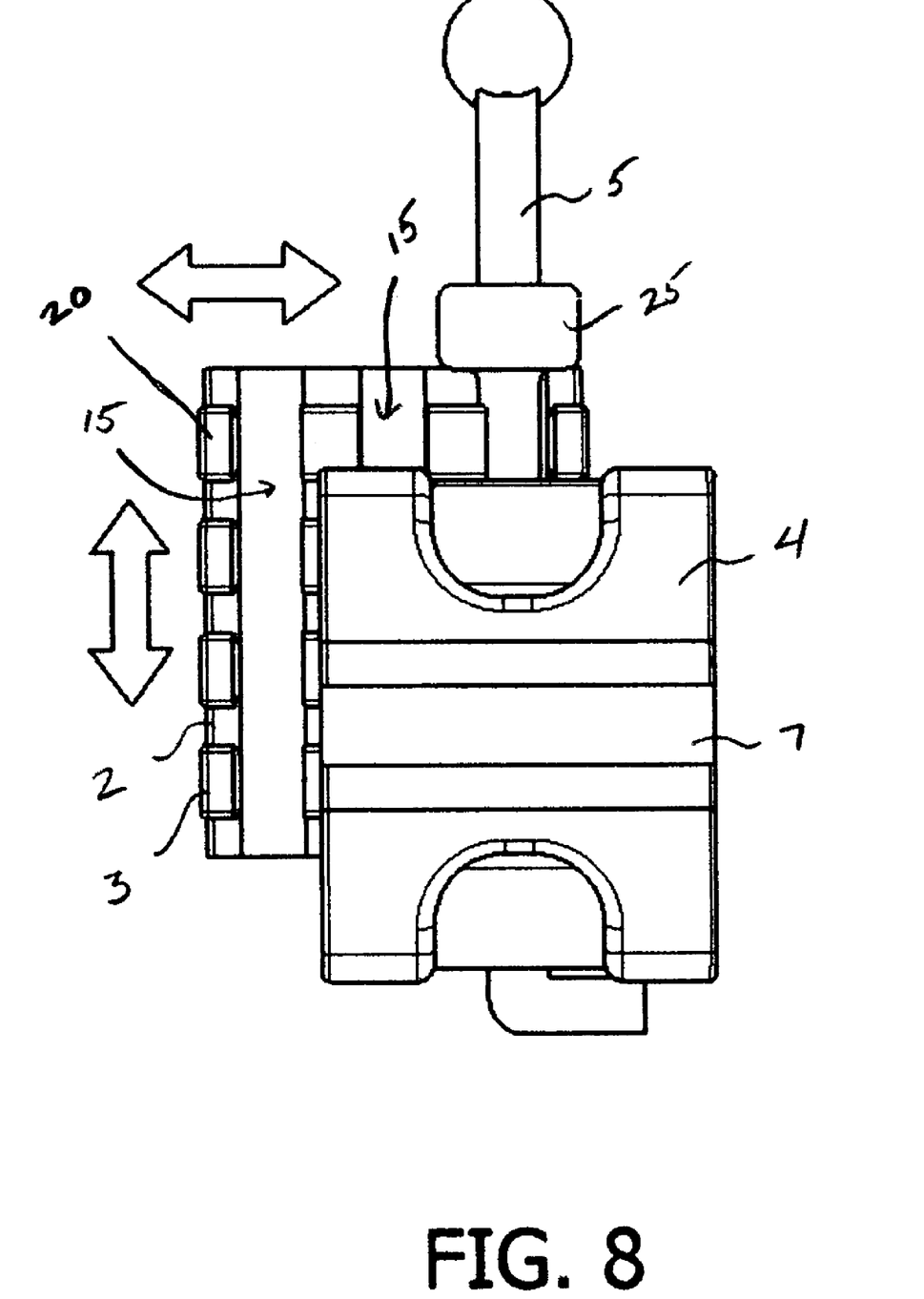
FIG. 8 is a frontal view of FIG. 7 showing the relationship and movement of the connecting plate relative to the base plate.

In another embodiment and as shown in FIGS. 7-8, the first device 3 of the second side 2b of the base plate 2 comprises a plurality of vertical and horizontal column of protrusions 20 and the second device 6 of the first side 4a of the connecting plate 4 comprises a plurality of vertical and horizontal column of protrusions 40, and the plurality of column of protrusions, 20 and 40 provides for a plurality of vertical and horizontal channels 15. The channels 15 provides the protrusion 20 and 40 to move during adjustment of the connecting plate 4 relative to the base plate 2 and the securing device 5 is situated with the channel 15 when the connecting plate 4 is locked into a certain position relative to the base plate 2. The protrusions 20 and 40 are designed to move vertically and horizontally within the channels 15 during the adjustment of the connecting plate 4 relative to the base plate 2. At least one of the protrusions 40 of the connecting plate 4 and at least one of the protrusions 20 of the base plate 2 engage one another when the securing device 5 locks the connecting plate 4 to the base plate 2.

The protrusions 20 and 40 of the base plate 2 and the connecting plate have geometric shapes, and at least one of the protrusions 20 of the base plate 2 has a geometric shape that creates a retentive undercut with the opposing geometric shape of at least one of the protrusions 40 of the connecting plate 4.

Figure 9:
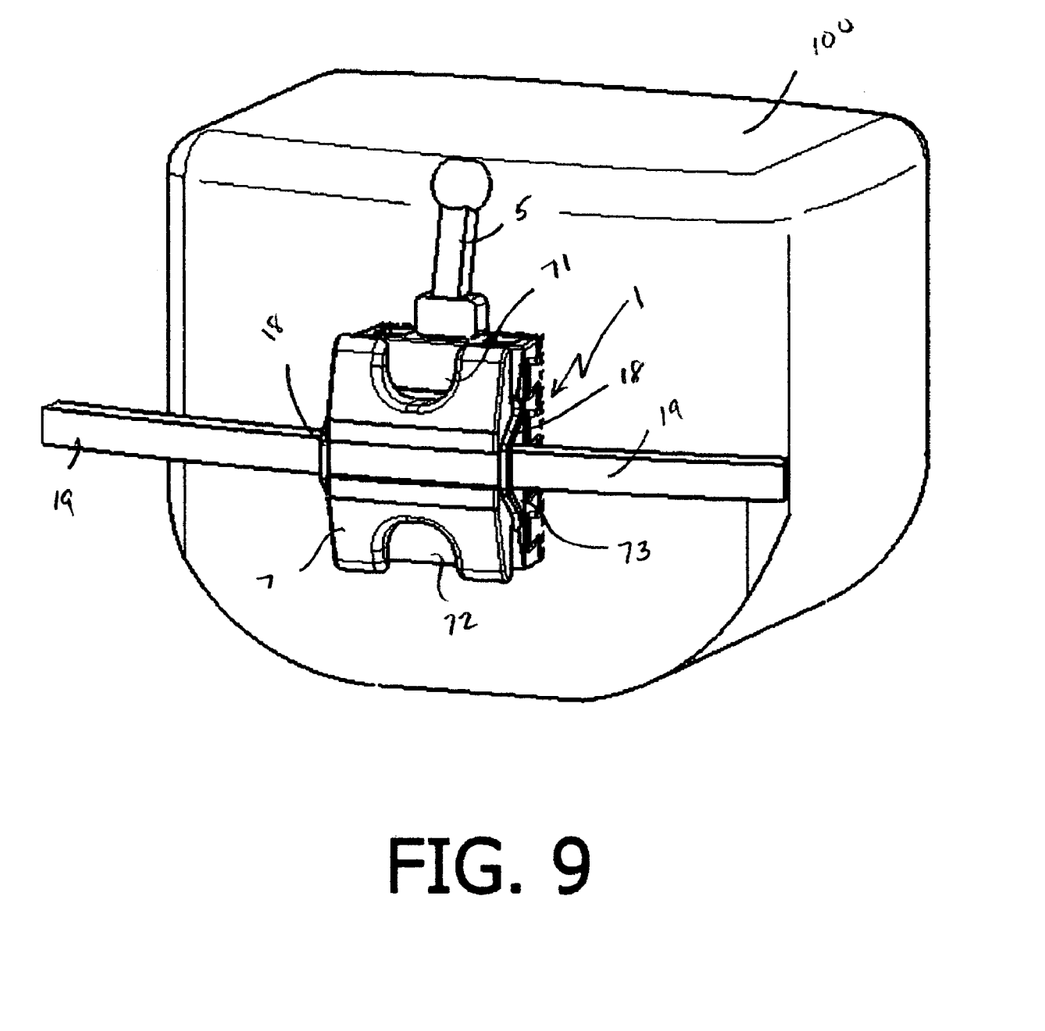
FIG. 9 is a perspective view of the orthodontic system of the present invention fully assembled on a patient's tooth.

FIG. 9 shows the orthodontic system 10 of the present invention assembled onto the tooth 100 of a patient. The tooth engaging side 2a of the base plate 2 is generally concave to conform with the curvature of a tooth 100. The orthodontic device 7 comprises at least two u-shaped protrusions, 71 and 72 respectively, on opposing ends 7a and 7b respectively; and a central cavity 73 for receiving a wire 19. At least one rubber band or steel ligature 18 is used to secure the wire 19 to the orthodontic device 7 within the cavity 73. The orthodontic device 7 is attached to the connecting plate 4 which is secured to the base plate 2 with the pin 5.

Figure 10:
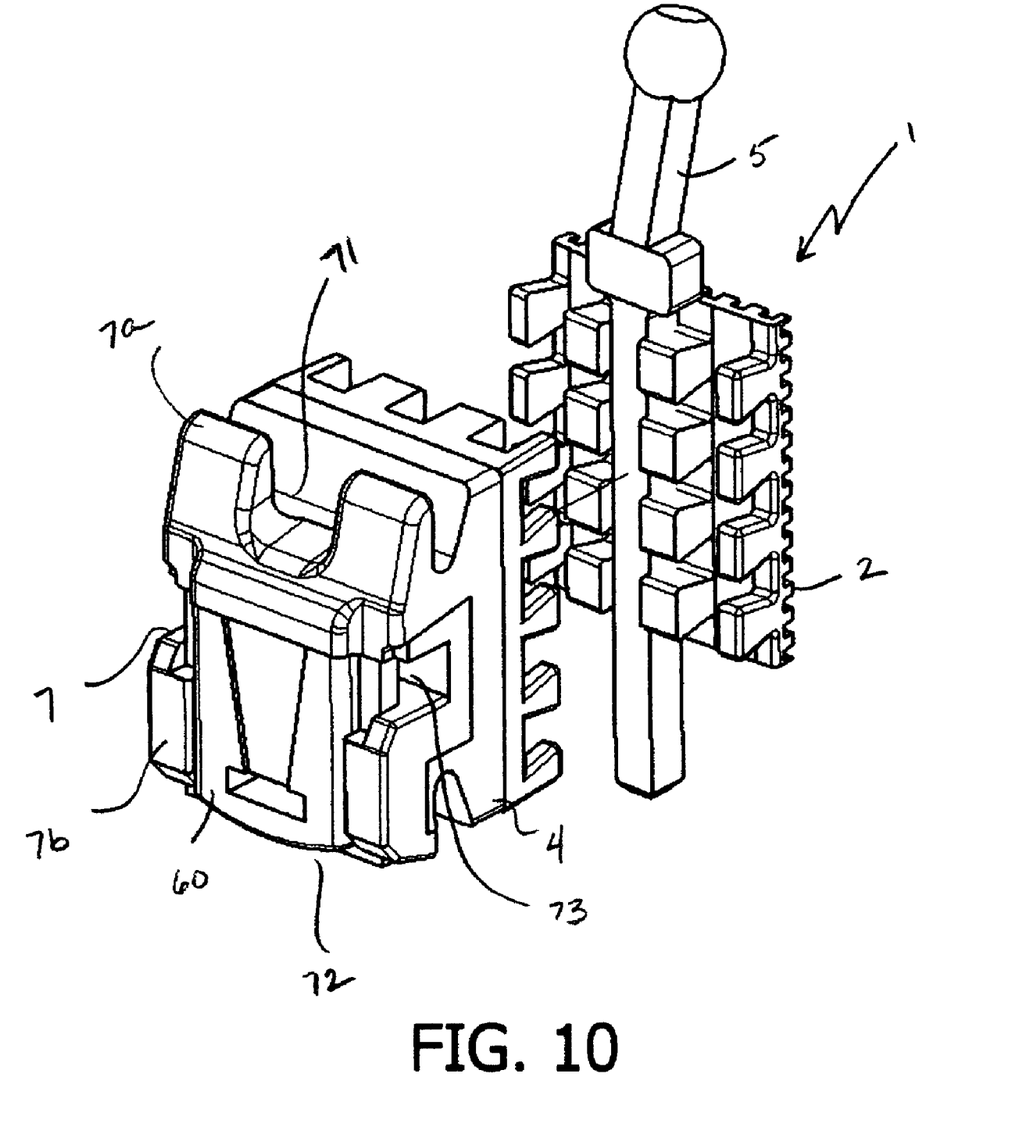
FIG. 10 depicts an exploded view of another embodiment of the orthodontic apparatus of the present invention with a connecting plate that has an opening and closing door.
Figure 11:
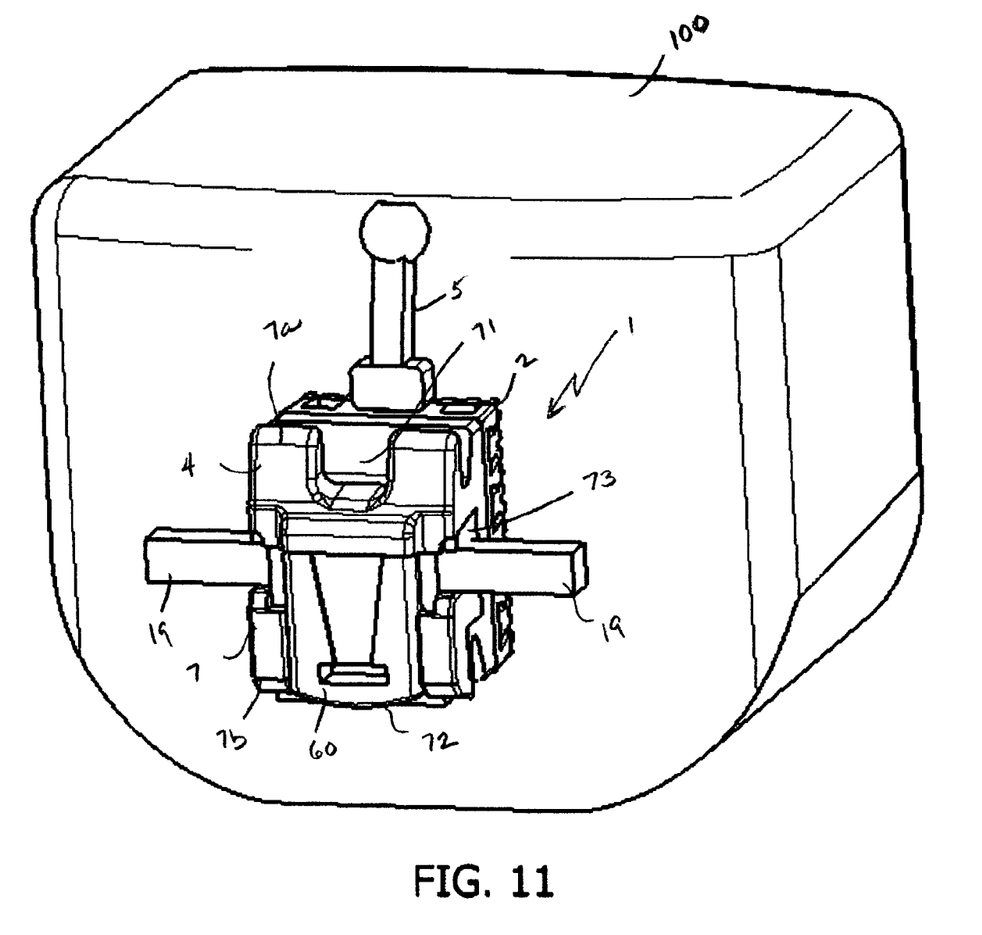
FIG. 11 is a perspective view of FIG. 9 fully assembled in a patient's tooth.
Figure 12:
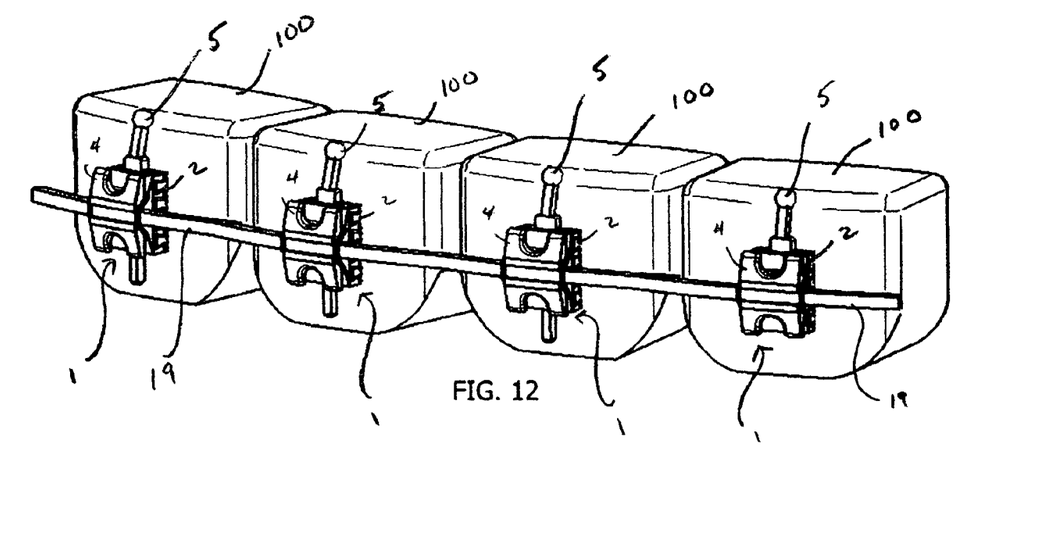
FIG. 12 is a perspective view of system of the present invention fully assembled in the patient's teeth.

FIGS. 10-12 depict another embodiment of the present invention wherein the orthodontic device 7 has a door 60 for enclosing the central cavity 73 to thereby lock the wire 19 into place. The orthodontic device 7 comprises at least two u-shaped protrusions, 71 and 72 respectively, on opposing ends 7a and 7b respectively; and a central cavity 73 for receiving a wire 19. The orthodontic device 7 is attached to the connecting plate 4 which is secured to the base plate 2 with the pin 5. FIGS. 11-12 shows the apparatus 1 assembled onto a patient's teeth 100.

Numerous modifications and variations of the present invention are possible in light of the above teachings. It is therefore to be understood that within the scope of the attendant claims attached hereto, this invention may be practiced otherwise than as specifically disclosed herein.

What is claimed is:

1. An adjustable orthodontic apparatus comprising:
 a base plate comprising opposing sides, a first side being a tooth engaging side and a second side comprising at least two base plate protrusions positioned in a height wise base plate axis and at least two base plate protrusions positioned in a widthwise base plate axis, the base plate protrusions having a plurality of base plate spaces between them forming intersecting base plate channels;
 a connecting plate having opposing sides, a first side comprising at least two connecting plate protrusions positioned in a height wise connecting plate axis and at least two connecting plate protrusions positioned in a widthwise connecting plate axis, the connecting plate protrusions having a plurality of connecting plate spaces between them forming intersecting connecting plate channels; and
 a securing device for locking the connecting plate to a desired position onto the base plate,
 wherein the base plate protrusions mechanically engage and are freely movable within the connecting plate channels and the connecting plate protrusions mechanically engage and are freely movable within the base plate channels while the base plate and the connecting plate are engaged, such that separation of the base plate and connecting plate can occur during an adjustment phase;
 the securing device mechanically engages a channel formed by the engaging base plate and connecting plate to prevent further free movement and separation once the desired position is obtained; and at least one of the protrusions of the base plate has a geometric shape that creates a retentive undercut with an opposing geometric shape of at least one of the protrusions of the connecting plate to form the mechanical engagement.

2. The apparatus of claim 1 wherein the securing device comprises a pin positioned in a height wise base plate axis.

3. The apparatus of claim 1 wherein a second side of said connecting plate comprises a surface for attaching an orthodontic device to said connecting device.

4. The apparatus of claim 1 wherein said tooth engaging side of said base plate is generally concave to conform with the curvature of a tooth.

5. An adjustable orthodontic apparatus comprising:
at least one base plate comprising opposing sides, a first side being a tooth engaging side and a second side comprising a plurality of columns of protrusions and plurality of intersecting channels created by the columns of protrusions;
at least one connecting plate having opposing sides, a first side comprising a plurality of columns of protrusions and plurality of intersecting channels created by the columns of protrusions, the protrusion designed to travel within the intersecting channels during an adjustment stage; and
a securing device for locking the connecting plate to a desired position onto the base plate;
wherein the protrusions mechanically engage and are freely movable within the intersecting channels while the base plate and the connecting plate are engaged, the mechanical engagement allowing separation of the base plate from the connecting plate during adjustment;
the securing device mechanically engages a channel formed by the engaging base plate and connecting plate to prevent further free movement and separation once the desired position is obtained; and
at least one of the protrusions of the base plate has a geometric shape that creates a retentive undercut with an opposing geometric shape of at least one of the protrusions of the connecting plate to form the mechanical engagement.

6. The apparatus of claim 5 wherein said securing device for locking said base plate to said connecting plate comprises a pin positioned in a height wise base plate axis.

7. The apparatus of claim 5 wherein a second side of said connecting plate comprises an orthodontic device.

8. An adjustable orthodontic system comprising:
a plurality of orthodontic apparati comprising at least one base plate comprising opposing sides, a first side being a tooth engaging side and a second side comprising a plurality of columns of protrusions and plurality of intersecting channels created by the columns of protrusions;
at least one connecting plate having opposing sides, a first side comprising a plurality of columns of protrusions and plurality of intersecting channels created by the columns of protrusions, the protrusion designed to travel within the intersecting channels during an adjustment stage, a second side comprising an orthodontic device; and a device for securing and locking the at least one connecting plate to a desired position onto the at least one base plate;
wherein the protrusions mechanically engage and are freely movable within the channels while the at least one base plate and the at least one connecting plate are engaged, the mechanical engagement allowing separation of the at least one base plate from the at least one connecting plate during the adjustment stage;
the securing device mechanically engages a channel formed by the engaging at least one base plate and at least one connecting plate to prevent further free movement and separation once the desired position is obtained; and
at least one of the protrusions of the base plate has a geometric shape that creates a retentive undercut with an opposing geometric shape of at least one of the protrusions of the connecting plate to form the mechanical engagement.

9. The system of claim 8 wherein said plurality of said apparati are attachable to a patient's teeth and each apparati are adjustable to desired positions and lockable into said desired positions using said securing device for attaching an archwire to each of said apparati.

10. The system of claim 8 wherein said device for securing and locking said base plate to said connecting plate comprises a pin positioned in a height wise base plate axis.

11. A method for adjusting an orthodontic apparatus comprising the steps of:
a. engaging a base plate to a tooth;
b. engaging a connecting plate to the base plate; and
c. adjusting the connecting plate relative to the base plate;
wherein
the base plate comprises opposing sides, a first side being a tooth engaging side and a second side comprising at least two base plate protrusions positioned in a height wise base plate axis and at least two base plate protrusions positioned in a widthwise base plate axis, the base plate protrusions having a plurality of base plate spaces between them forming intersecting base plate channels;
the connecting plate comprises opposing sides, a first side comprising at least two connecting plate protrusions positioned in a height wise connecting plate axis and at least two connecting plate protrusions positioned in a widthwise connecting plate axis, the connecting plate protrusions having a plurality of connecting plate spaces between them forming intersecting connecting plate channels; and
a securing device locks the connecting plate to a desired position onto the base plate,
wherein the base plate protrusions mechanically engage and are freely movable within the connecting plate channels and the connecting plate protrusions mechanically engage and are freely movable within the base plate channels while the base plate and the connecting plate are engaged, the mechanical engagement allowing separation of the base plate from the connecting plate during an adjustment phase;
the securing device mechanically engages a channel formed by the engaging base plate and connecting plate to prevent further free movement and separation once the desired position is obtained; and
at least one of the protrusions of the base plate has a geometric shape that creates a retentive undercut with an opposing geometric shape of at least one of the protrusions of the connecting plate to form the mechanical engagement.

12. The method of claim 11 wherein the securing device comprises a pin positioned in a height wise base plate axis.

13. The method of claim 11 wherein a second side of the connecting plate comprises a surface for attaching an orthodontic device to the connecting device.

* * * * *